US012751640B2

(12) United States Patent
Wang et al.

(10) Patent No.: US 12,751,640 B2
(45) Date of Patent: Oct. 6, 2026

(54) RADAR HEARTBEAT SIGNAL DETECTION BASED ON PRT MODEL SHAPING

(71) Applicant: NATIONAL SUN YAT-SEN UNIVERSITY, Kaohsiung (TW)

(72) Inventors: Fu-Kang Wang, Kaohsiung (TW); Ju-Yin Shih, Kaohsiung (TW); Ji-Xun Zhong, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 0 days.

(21) Appl. No.: 19/300,957

(22) Filed: Aug. 15, 2025

(65) Prior Publication Data

US 2026/0165596 A1 Jun. 18, 2026

(30) Foreign Application Priority Data

Dec. 18, 2024 (TW) ................................ 113149492

(51) Int. Cl.
*A61B 5/05* (2021.01)
*A61B 5/00* (2006.01)
*A61B 5/024* (2006.01)

(52) U.S. Cl.
CPC ................ *A61B 5/05* (2013.01); *A61B 5/024* (2013.01); *A61B 5/7246* (2013.01); *A61B 5/725* (2013.01)

(58) Field of Classification Search
None
See application file for complete search history.

(56) References Cited

U.S. PATENT DOCUMENTS

2024/0379223 A1 11/2024 Tsushima et al.

FOREIGN PATENT DOCUMENTS

CN 112168152 A 1/2021
WO WO-2024186741 A1 * 9/2024 .......... A61B 5/7246

OTHER PUBLICATIONS

Fernández et al., "FMM: An R Package for Modeling Rhythmic Patterns in Oscillatory Systems" (Jun. 20, 2022). The R Journal, 14( 1), 361-380. (Year: 2022).*

Rueda et al., "A unique cardiac electrocardiogramodel. Toward interpretable AI diagnosis," (Dec. 22, 2022) iScience, vol. 25, Issue 12, Dec. 22, 2022, 105617. (Year: 2022).*

Rueda et al., "The hidden waves in the ECG uncovered revealing a sound automated interpretation method," (Feb. 12, 2021), Sci Rep. Feb. 12, 2021;11:3724. (Year: 2021).*

(Continued)

*Primary Examiner* — Keith M Raymond
*Assistant Examiner* — Ashish S. Jasani
(74) *Attorney, Agent, or Firm* — Demian K. Jackson; Jackson IPG PLLC

(57) ABSTRACT

In radar heartbeat signal detection based on PRT model shaping, a vital-sign signal including a heartbeat component and a respiration component is detected by a radar and sent to a computing device which is electrically connected to the radar, the computing device extracts the heartbeat component from the vital-sign signal to obtain a radar heartbeat signal and segments the radar heartbeat signal into two or more one-cycle radar heartbeat signals, and the computing device multiply each of the one-cycle radar heartbeat signal with a PRT model and connects the one-cycle radar heartbeat signals as a shaped radar heartbeat signal.

17 Claims, 5 Drawing Sheets

(56) References Cited

OTHER PUBLICATIONS

Rueda et al., "The FMM Approach to Analyze Biomedical Signals: Theory, Software, Applications and Future," (May 19, 2021), Mathematics 2021, 9(10), 1145. (Year: 2021).*
Ju-Yin Shih et al., PRT Shaping Method for Heart Rate Variability Monitoring Using Phase- and Quadrature Self-Injection-Locked (PQSIL) Radar, IEEE Transactions on Microwave Theory and Techniques, Aug. 15, 2024.
Taiwanese office action mailed Apr. 7, 2025 for Taiwanese patent application No. 113149492, 3 pages.

* cited by examiner

RADAR HEARTBEAT SIGNAL DETECTION BASED ON PRT MODEL SHAPING

CROSS-REFERENCE TO RELATED APPLICATIONS

This application claims priority to R.O.C patent application No. 113149492 filed Dec. 18, 2024, the disclosure of which is hereby incorporated by reference in its entirety.

FIELD OF THE INVENTION

This invention relates to a radar heartbeat signal detection, and more particularly to a radar heartbeat signal detection based on PRT model shaping.

BACKGROUND OF THE INVENTION

Heart rate variability (HRV) is a measurement of variation in time between each heartbeat, it has become an important index for human healthy recently and also important for athletes to train effectively. HRV is signified by RR intervals (RRIs) of electrocardiogram (ECG) usually. ECG-based HRV analysis requires long-term attachment of electrode patches to the subject, causing discomfort during the measurement. Noncontact sensors can be used for HRV monitoring. However, noncontact sensors are easily interfered by subject's respiration motion and noise to produce less accurate heart rate compared with ECG devices, and they are not capable of stable HRV analysis. Accuracy of short-term heart rate results measured by the noncontact sensors can be increased after spectrum analysis, but the resolution is still inadequate, otherwise, long-term heart rate measurement cannot be utilized for real-time HRV monitoring. Consequently, how to achieve high-accuracy noncontact heart rate measurement is critical for noncontact HRV analysis.

SUMMARY OF THE INVENTION

One object of the present invention is to shape a radar heartbeat signal via a PRT model to obtain a high-accuracy shaped radar heartbeat signal.

A radar heartbeat signal detection based on PRT model shaping includes the steps of vital-sign signal detection, heartbeat component extraction, one-cycle segmentation and PRT shaping. A radar detects a vital-sign signal including a heartbeat component and a respiration component, and it transmits the vital-sign signal to a computing device which is electrically connected to the radar. The computing device extracts the heartbeat component from the vital-sign signal to get a radar heartbeat signal, segments the radar heartbeat signal into multiple one-cycle radar heartbeat signals, multiply each of the one-cycle radar heartbeat signals with a PRT model and combines the one-cycle radar heartbeat signals to become a shaped radar heartbeat signal.

Through heartbeat component extraction, one-cycle segmentation and PRT model shaping process of the present invention, the heartbeat signal obtained by noncontact detection can be identical to ECG signals for accurate HRV monitoring.

DETAILED DESCRIPTION OF THE INVENTION

Figure 1:
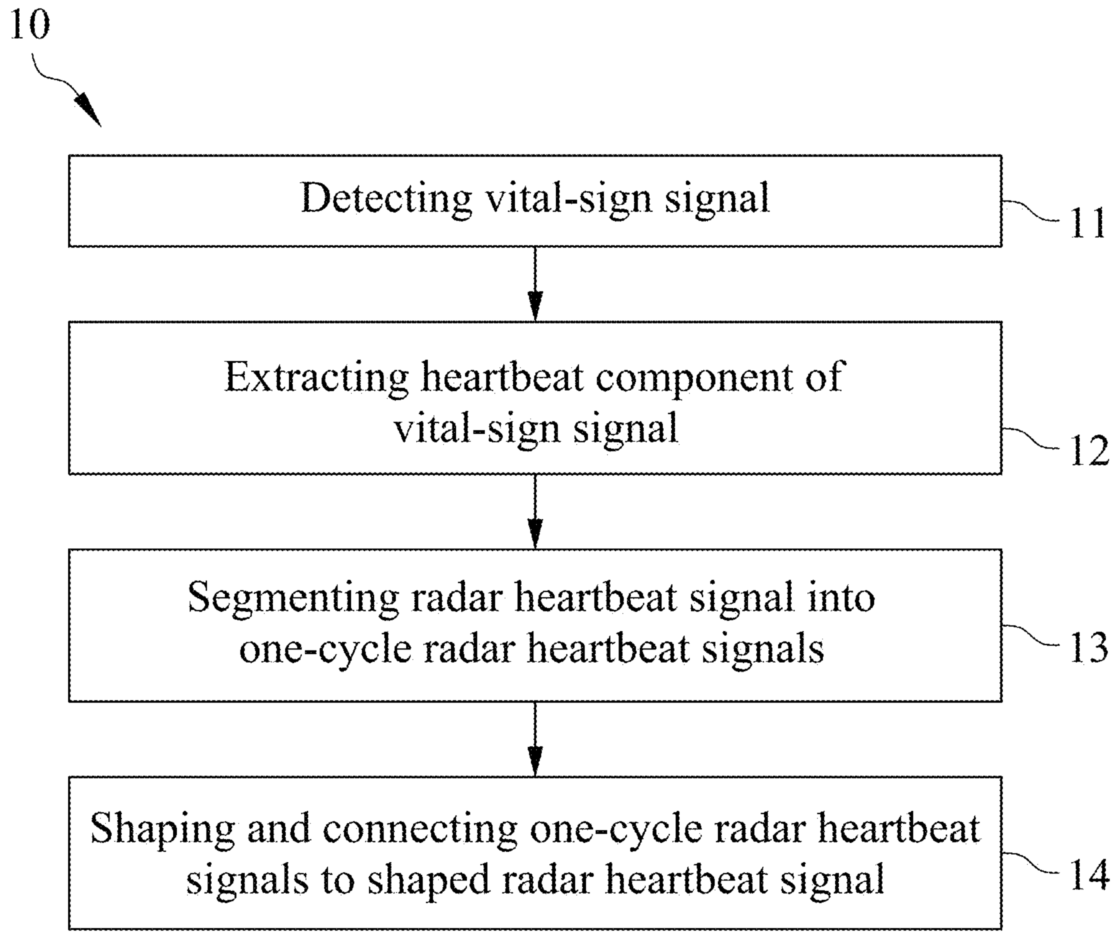
FIG. 1 is a flow chart illustrating a radar heartbeat signal detection based on PRT model shaping in accordance with one embodiment of the present invention.

FIG. 1 is a flow chart illustrating a radar heartbeat signal detection 10 based on PRT model shaping in accordance with one embodiment of the present invention. The radar heartbeat signal detection 10 includes a step 11 of detecting a vital-sign signal, a step 12 of extracting a heartbeat component in the vital-sign signal, a step 13 of segmenting a radar heartbeat signal into one-cycle radar heartbeat signals, and a step 14 of shaping and connecting the one-cycle radar heartbeat signals to become a shaped radar heartbeat signal.

Figure 2:
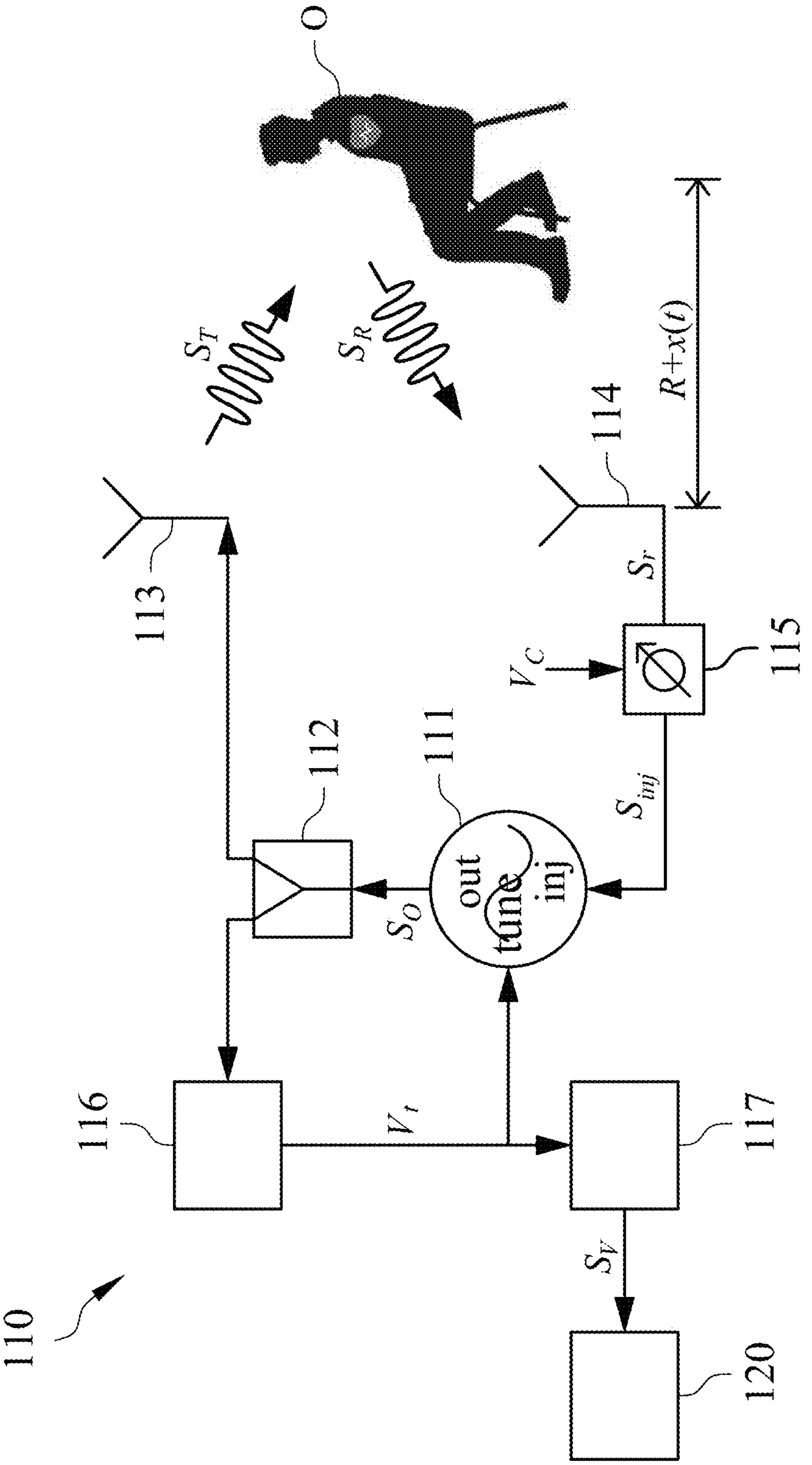
FIG. 2 is a circuit diagram illustrating a radar and a computing device in accordance with one embodiment of the present invention.

With reference to FIGS. 1 and 2, a vital-sign signal $S_V$ is detected by a radar 110 in the step 11 and it contains a heartbeat component and a respiration component. As shown in FIG. 2, the radar 110 of this embodiment is a phase- and quadrature self-injection-locked (PQSIL) radar and includes a self-injection-locked oscillator (SILO) 111, a power splitter 112, a transmit antenna 113, a receive antenna 114, a phase shifter 115, a phase-lock loop (PLL) circuit 116 and a processor 117. An oscillation signal $S_O$ is output from the SILO 111 to the power splitter 112 and is split into two parts by the power splitter 112. Two parts of the oscillation signal $S_O$ are sent to the transmit antenna 113 and the PLL circuit 116, respectively. The transmit antenna 113 transmits the oscillation signal $S_O$ as a transmitted signal $S_T$ to a subject O, and the receive antenna 114 receives a reflected signal $S_R$ from the subject O as a received signal $S_r$, and the received signal $S_r$ is sent to the phase shifter 115. The phase shifter 115 receives a control signal $V_C$ to delay the received signal $S_r$ with phase delay. In this embodiment, the phase shifter 115 is controlled by the control signal $V_C$ to delay the received signal $S_r$ with 0 and 90 degrees phase delays and produce a self-injection-locked (SIL) signal $S_{inj}$ operating in two modes, and the SIL signal $S_{inj}$ is injected into the SILO 111 to make the SILO 111 enter a self-injection-locked state. The SILO 111 of this embodiment is locked in two phase modes by the phase delay of the phase shifter 115, accordingly, waveform distortion can be eliminated in back-end circuit through signal processing to solve null-point problem of the SIL radar.

The PLL circuit 116 is electrically connected to the power splitter 112 to receive the other part of the oscillation signal $S_O$. The PLL circuit 116 detects phase variation in the oscillation signal $S_O$ using a received reference signal (not shown) to generate a voltage tuning signal $V_t$. The voltage tuning signal $V_t$ is sent back to the SILO 111 to stabilize output frequency of the SILO 111.

Figure 3:
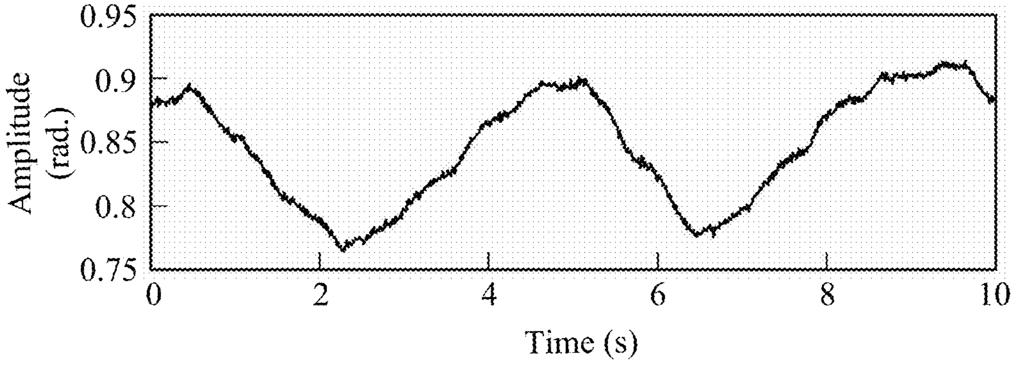
FIG. 3 shows waveform of a vital-sign signal detected by a radar in accordance with one embodiment of the present invention.

With reference to FIG. 2, the reflected signal $S_R$ is phase-modulated due to the Doppler effect caused by movements of the subject O relative to the radar 110, and the received signal $S_r$ and the SIL signal $S_{inj}$ also have the phase modulation, thus, output frequency of the SILO 111 is shifted as the SILO 111 is injection-locked by the SIL signal $S_{inj}$. Owing to the voltage tuning signal $V_t$ produced by the PLL circuit 116 according to the phase difference can be used to eliminate the frequency shift of the SILO 111, voltage variation of the voltage tuning signal $V_t$ can exhibit the Doppler phase shift induced by movements of the subject O. The processer 117 is electrically connected to the PLL circuit 116 to receive and process the voltage tuning signal $V_t$ to obtain the vital-sign signal $S_V$ of the subject O. As shown in FIG. 2, the subject O is almost still and seated in front of the radar 110 at a distance R, movements x(t) of the subject O relative to the radar 110 result from respiration, heartbeat, small random body movement and noise interference so the vital-sign signal $S_V$ contains the components of both heartbeat and respiration movements. FIG. 3 shows experiment result of the measured vital-sign signal $S_V$ which involves the heartbeat component, the respiration component, small random motion of the subject O and noise.

Figure 4:
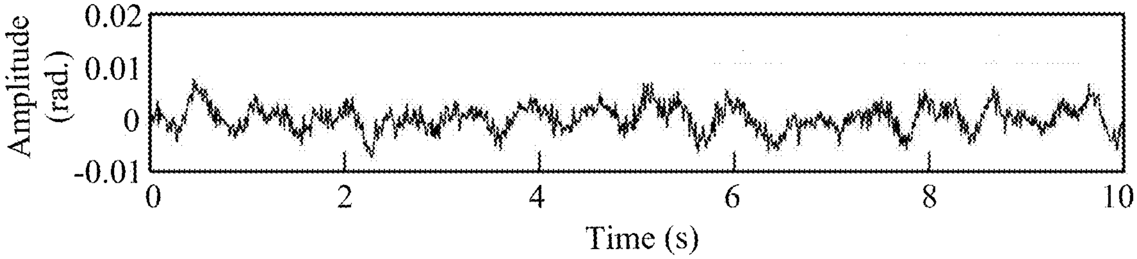
FIG. 4 shows waveform of a residual vital-sign signal yielded by a computing device in accordance with one embodiment of the present invention.

With reference to FIGS. 1 and 2, in the step 12, a computing device 120 electrically connected to the radar 110 is provided to receive the vital-sign signal $S_V$ and extract the heartbeat component from the vital-sign signal $S_V$ to get a radar heartbeat signal. The computing device 120 and the processor 117 are shown as two blocks in FIG. 2, but they may be two programs in a computation equipment, e.g. desktop computer, laptop computer or microprocessor able to perform logical operation. In order to achieve high-accuracy heartbeat signal detection, the heartbeat component in the vital-sign signal $S_V$ is extracted to get the radar heartbeat signal in the step 12. In this embodiment, the computing device 120 uses a filter to filter the vital-sign signal $S_V$ and get the respiration component in the vital-sign signal $S_V$, then the computing device 120 removes the respiration component from the vital-sign signal $S_V$ to yield a residual vital-sign signal which includes the heartbeat component. Owing to the heartbeat component has higher frequency than the respiration component, it is available to extract the heartbeat component with higher frequency from the vital-sign signal $S_V$ directly using a high-pass filter, but a part of the heartbeat component may be removed by the high-pass filter which has more complex architecture than low-pass filter. Preferably, a low-pass filter is used in this embodiment, the respiration component is filter out from the vital-sign signal $S_V$ by the low-pass filter and then is removed from the vital-sign signal $S_V$ to obtain the residual vital-sign signal including the heartbeat component only. This respiration removal method can lower circuit complexity significantly and avoid the heartbeat component from being removed. As shown in FIG. 4, which is the waveform of the residual vital-sign signal measured in this embodiment, there are the components with higher frequency and noises in the residual vital-sign signal.

Figure 5:
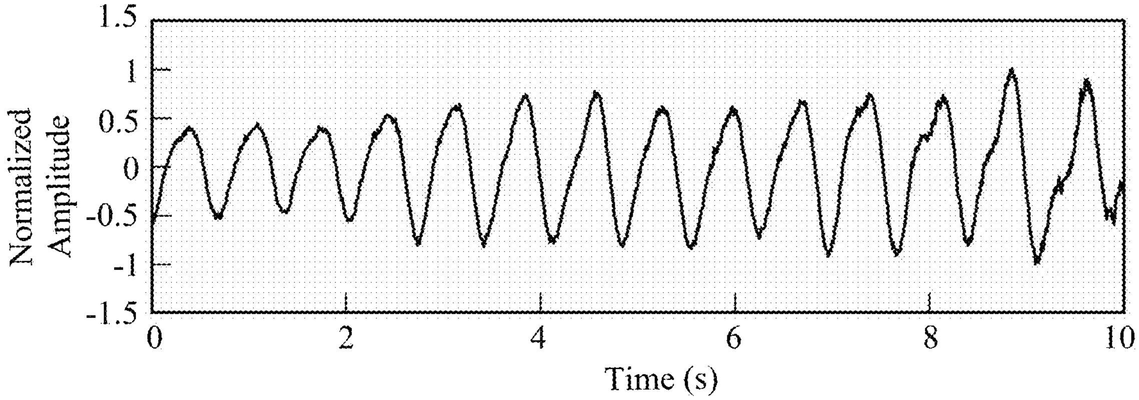
FIG. 5 shows waveform of a radar heartbeat signal obtained by a computing device after autocorrelation process in accordance with one embodiment of the present invention.

The residual vital-sign signal still has the noises, so the computing device 120 applies an autocorrelation process on the residual vital-sign signal to obtain the radar heartbeat signal. The autocorrelation process is shown as $$S_{hr}(\tau)=\frac{1}{T}\int_0^T S_{res}(t)S_{res}(t-\tau)dt$$

where $S_{hr}(\tau)$ is the radar heartbeat signal, $S_{res}(t)$ is the residual vital-sign signal, and $\tau$ is a delay time. The autocorrelation process can substantially reduce non-periodic features in the residual vital-sign signal to obtain clear periodic features. Accordingly, via the autocorrelation technique, the non-periodic features (e.g. noises) in the residual vital-sign signal can be eliminated and the periodic features (e.g. the heartbeat component) in the residual vital-sign signal can be enhanced. FIG. 5 shows the waveform of the radar heartbeat signal obtained after the autocorrelation process, the radar heartbeat signal exhibits a noise-free waveform.

Figure 6:
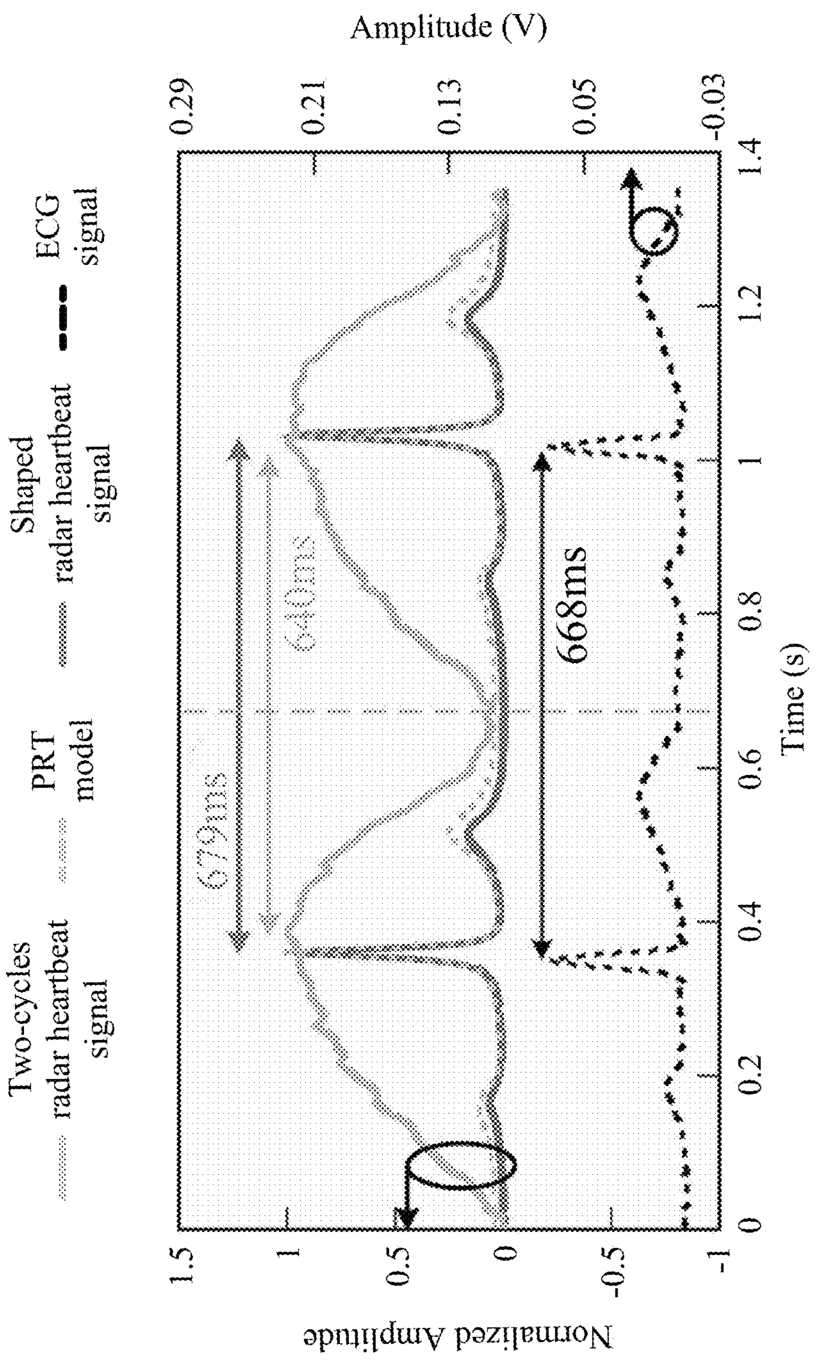
FIG. 6 shows waveforms of an ECG signal and a two-cycle radar heartbeat signal, a PRT model, a shaped radar heartbeat signal which are obtained by a computing device in accordance with one embodiment of the present invention.

With reference to FIGS. 1 and 2, in the step 13, the computing device 120 segments the radar heartbeat signal into multiple one-cycle radar heartbeat signals and shapes the one-cycle radar heartbeat signals, respectively. Peaks of the radar heartbeat signal are easily interfered by the noises to cause an error, as a result, the computing device 120 segments the radar heartbeat signal into the one-cycle radar heartbeat signals at valleys in this embodiment. Referring to FIG. 6, the radar heartbeat signal is segmented into two one-cycle radar heartbeat signals in the embodiment.

Figure 7:
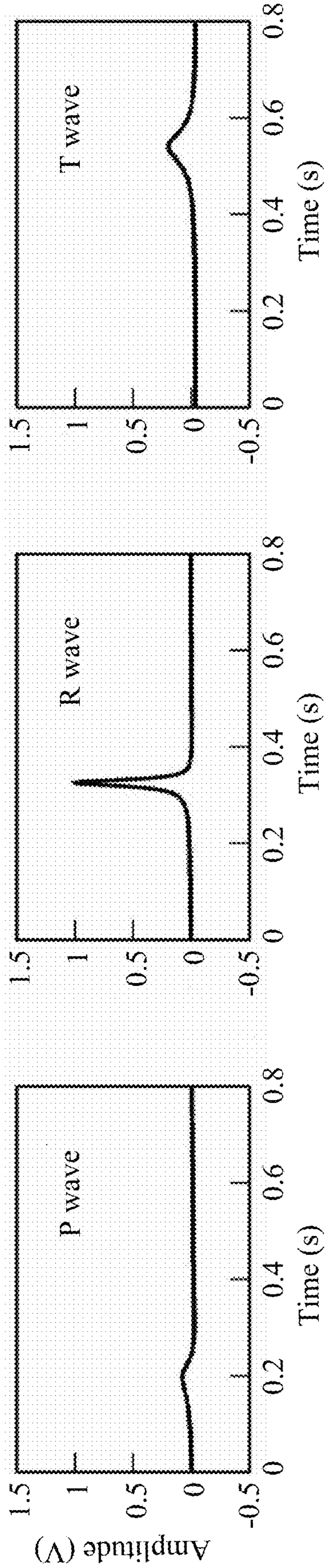
FIG. 7 shows waveforms of P, R and T waves in PRT model in accordance with one embodiment of the present invention.

With reference to FIGS. 1 and 2, each of the one-cycle radar heartbeat signals is multiplied with a PRT model and connected to become a shaped radar heartbeat signal by the computing device 120 in the step 14. In this embodiment, the PRT model is developed based on frequency modulation möbius (FMM) model. After short-term ECG recording of the subject O, P, R and T waves in the ECG signal are fitted with the FMM model, respectively, to get P, R and T waves of the FMM model, and P, R and T waves of the FMM model are combined into the PRT model. FIG. 7 represents P, R and T waveforms of FMM model after fitting, and the PRT model can be expressed as $$PRT(t)=\sum_{i\in\{P,R,T\}} W_i(t, A_i, \alpha_i, \beta_i, \omega_i)$$

where P, R and T denote P wave, R wave and T wave, respectively, $W_i(t, A_i, \alpha_i, \beta_i, \omega_i)$ denotes the FMM model, A is the wave amplitude, $\alpha$ is the location parameter, $\beta$ is the skewness, $\omega$ is the kurtosis, and the FMM model can be expressed as $$W(t, A, \alpha, \beta, \omega)=A\cos(\phi(t, \alpha, \beta, \omega))$$

where $\phi(t, \alpha, \beta, \omega)$ is the wave phase and can be expressed $$\phi(t, \alpha, \beta, \omega)=\beta+2\tan^{-1}\left(\omega\left(\frac{1-\alpha}{2}\right)\right).$$

In this embodiment, only calculations of P, R and T waves of the FMM model are required so short-term ECG recording (e.g. 5-s ECG measurement) can be used for fitting the FMM model to prevent discomfort of the subject due to long-term attachment of electrode patches.

Multiplication of each of the one-cycle radar heartbeat signals with the PRT model can be expressed as $$S_{shaped}(t)=S_{cycle}(\tau)\cdot PRT(t)$$

where $S_{shaped}(t)$ is a one-cycle shaped radar heartbeat signal, $S_{cycle}(\tau)$ is the one-cycle radar heartbeat signal, and PRT(t) is the PRT model. And the shaped radar heartbeat signal is got after combining the one-cycle shaped radar heartbeat signals.

With reference to FIG. 6, the ECG signal and the shaped radar heartbeat signal which is obtained via the PRT model shaping process have similar waveforms with the HRV error being only 4 ms, less than the HRV error of 28 ms between the ECG signal and the one-cycle radar heartbeat signal without shaping process. Accordingly, the present invention can improve accuracy of noncontact HRV monitoring significantly. By comparison between the reference ECG signals and the shaped radar heartbeat signals of multiple experimental results, the radar heartbeat signal detection 10 of the present invention can reduce errors in mean relative error (MRE) and root-mean-square error (RMSE) to 1.97% and 20.2 ms, respectively, and can increase 5 beats per minute (5-bpm) accuracy to 100%, indicating relatively low errors compared with the ECG signals. The present invention can detect the shaped radar heartbeat signals having consistent performances with the reference ECG signals using uncomplicated computation, thus, it can be utilized for real-time noncontact HRV monitoring.

Through the steps of heartbeat component extraction, one-cycle radar heartbeat signal segmentation and PRT model shaping process, the present invention can detect high-accuracy heartbeat signals compared with the reference ECG signals for noncontact HRV monitoring.

The scope of the present invention is only limited by the following claims. Any alternation and modification without departing from the scope and spirit of the present invention will become apparent to those skilled in the art.

The invention claimed is:

1. A radar heartbeat signal detection based on PRT model shaping comprising the steps of:

- detecting a vital-sign signal by a radar, the vital-sign signal includes a heartbeat component and a respiration component;
- receiving the vital-sign signal and extracting the heartbeat component in the vital-sign signal to obtain a radar heartbeat signal by a computing device which is electrically connected to the radar;
- segmenting the radar heartbeat signal into a plurality of one-cycle radar heartbeat signals by the computing device; and
- multiplying each of the plurality of one-cycle radar heartbeat signals with a PRT model and connecting the plurality of one-cycle radar heartbeat signals to obtain a shaped radar heartbeat signal by the computing device.

2. The radar heartbeat signal detection based on PRT model shaping in accordance with claim 1, wherein the computing device is configured to filter the vital-sign signal by a filter to obtain the respiration component in the vital-sign signal and is configured to remove the respiration component from the vital-sign signal to obtain a residual vital-sign signal, the residual vital-sign signal includes the heartbeat component.

3. The radar heartbeat signal detection based on PRT model shaping in accordance with claim 2, wherein the filter is a low-pass filter.

4. The radar heartbeat signal detection based on PRT model shaping in accordance with claim 2, wherein the computing device is configured to apply an autocorrelation process on the residual vital-sign signal to obtain the radar heartbeat signal.

5. The radar heartbeat signal detection based on PRT model shaping in accordance with claim 4, wherein the autocorrelation process is represented by an equation as follows:

$$S_{hr}(\tau)=\frac{1}{T}\int_0^T S_{res}(t)S_{res}(t-\tau)dt$$

where $S_{hr}(\tau)$ represents the radar heartbeat signal, $S_{res}(t)$ represents the residual vital-sign signal, and $\tau$ represents a delay time.

6. The radar heartbeat signal detection based on PRT model shaping in accordance with claim 5, wherein the computing device is configured to segment the radar heartbeat signal into the plurality of one-cycle radar heartbeat signals at valleys.

7. The radar heartbeat signal detection based on PRT model shaping in accordance with claim 6, wherein multiplication of each of the plurality of one-cycle radar heartbeat signals with the PRT model is expressed as:

$$S_{shaped}(\tau)=S_{cycle}(\tau)\cdot PRT(t)$$

where $S_{shaped}(\tau)$ is a one-cycle shaped radar heartbeat signal, $S_{cycle}(\tau)$ is the one-cycle radar heartbeat signal, and PRT(t) is the PRT model.

8. The radar heartbeat signal detection based on PRT model shaping in accordance with claim 7, wherein the PRT model is expressed as:

$$PRT(t)=\sum_{i\in\{P,R,T\}} W_i(t, A_i, \alpha_i, \beta_i, \omega_i)$$

where P is P wave, R is R wave, Tis T wave, $W_i(t, A_i, \alpha_i, \beta_i, \omega_i)$ is a frequency modulation möbius (FMM) model, A is a wave amplitude, $\alpha$ is a location parameter, $\beta$ is a skewness, and $\omega$ is a kurtosis.

9. The radar heartbeat signal detection based on PRT model shaping in accordance with claim 8, wherein the FMM model is expressed as:

$$W(t, A, \alpha, \beta, \omega)=A\cos(\phi(t, \alpha, \beta, \omega))$$

where $\phi(t, \alpha, \beta, \omega)$ is a wave phase and is expressed as $$\phi(t, \alpha, \beta, \omega)=\beta+2\tan^{-1}\left(\omega\left(\frac{1-\alpha}{2}\right)\right).$$

10. The radar heartbeat signal detection based on PRT model shaping in accordance with claim 9, wherein $W_i(t, A_i, \alpha_i, \beta_i, \omega_i)$ is obtained by fitting P, R and T waves in a ECG signal of a subject.

11. The radar heartbeat signal detection based on PRT model shaping in accordance with claim 8, wherein $W_i(t, A_i, \alpha_i, \beta_i, \omega_i)$ is obtained by fitting P, R and T waves in a ECG signal of a subject.

12. The radar heartbeat signal detection based on PRT model shaping in accordance with claim 1, wherein the computing device is configured to segment the radar heartbeat signal into the plurality of one-cycle radar heartbeat signals at valleys.

13. The radar heartbeat signal detection based on PRT model shaping in accordance with claim 12, wherein multiplication of each of the plurality of one-cycle radar heartbeat signals with the PRT model is expressed as:

$$S_{shaped}(\tau) = S_{cycle}(\tau) \cdot PRT(t)$$

where $S_{shaped}(\tau)$ is a one-cycle shaped radar heartbeat signal, $S_{cycle}(\tau)$ is the one-cycle radar heartbeat signal, and PRT(t) is the PRT model.

14. The radar heartbeat signal detection based on PRT model shaping in accordance with claim 13, wherein the PRT model is expressed as:

$$PRT(t) = \sum_{i \in \{P,R,T\}} W_i(t, A_i, \alpha_i, \beta_i, \omega_i)$$

where P is P wave, R is R wave, T is T wave, $\omega_i(t, A_i, \alpha_i, \beta_i, \omega_i)$ is a frequency modulation möbius (FMM) model, A is a wave amplitude, α is a location parameter, β is a skewness, and ω is a kurtosis.

15. The radar heartbeat signal detection based on PRT model shaping in accordance with claim 14, wherein the FMM model is expressed as:

$$W(t, A, \alpha, \beta, \omega) = A\cos(\phi(t, \alpha, \beta, \omega))$$

where $\phi(t, \alpha, \beta, \omega)$ is a wave phase and is expressed as $$\phi(t, \alpha, \beta, \omega) = \beta + 2\tan^{-1}\left(\omega\left(\frac{1-\alpha}{2}\right)\right).$$

16. The radar heartbeat signal detection based on PRT model shaping in accordance with claim 15, wherein $W_i(t, A_i, \alpha_i, \beta_i, \omega_i)$ is obtained by fitting P, R and T waves in a ECG signal of a subject.

17. The radar heartbeat signal detection based on PRT model shaping in accordance with claim 14, wherein $W_i(t, A_i, \alpha_i, \beta_i, \omega_i)$ is obtained by fitting P, R and T waves in a ECG signal of a subject.

* * * * *